United States Patent
Liu et al.

(10) Patent No.: US 8,859,995 B2
(45) Date of Patent: Oct. 14, 2014

(54) END OF SERVICE LIFE INDICATOR FOR ORGANIC VAPOR RESPIRATOR FILTER CARTRIDGE

(75) Inventors: Hailin Liu, Shanghai (CN); Tao Pan, Shanghai (CN); Xuanbin Liu, Shanghai (CN); Li Wang, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 264 days.

(21) Appl. No.: 13/536,019

(22) Filed: Jun. 28, 2012

(65) Prior Publication Data

US 2014/0001376 A1    Jan. 2, 2014

(51) Int. Cl.
  *G01J 1/58* (2006.01)
(52) U.S. Cl.
  USPC .................................. 250/458.1; 250/459.1
(58) Field of Classification Search
  USPC .................................. 250/458.1, 459.1, 372
  See application file for complete search history.

(56) References Cited

U.S. PATENT DOCUMENTS

| | | | |
|---|---|---|---|
| 4,053,051 | A | 10/1977 | Brinkhoff |
| 4,434,794 | A | 3/1984 | Leight |
| 4,737,343 | A | 4/1988 | Hirschfeld |
| 4,774,938 | A | 10/1988 | Leight |
| 5,659,296 | A | 8/1997 | Debe et al. |
| 6,701,864 | B2 | 3/2004 | Watson, Jr. et al. |
| 7,503,962 | B2 | 3/2009 | Attar |
| 7,592,184 | B2 | 9/2009 | Khalil et al. |
| 2003/0051939 | A1 | 3/2003 | Werblud |
| 2004/0045558 | A1 | 3/2004 | Taylor et al. |
| 2005/0056289 | A1 | 3/2005 | Jenkins, Jr. et al. |
| 2006/0162992 | A1 | 7/2006 | Seville |
| 2006/0175722 | A1 | 8/2006 | Babcock et al. |
| 2007/0221232 | A1 | 9/2007 | Jenkins |
| 2008/0063575 | A1 | 3/2008 | Rakow et al. |
| 2010/0284010 | A1 | 11/2010 | Duncan et al. |

FOREIGN PATENT DOCUMENTS

WO    2011123411 A1    10/2011

OTHER PUBLICATIONS

Favas, George; "End of Service Life Indicator (ESLI) for Respirator Cartridges. Part 1: Literature Review"; Australian Government—Department of Defence; Document No. DSTO-TN-0657; pp. 1-49, Jul. 2005.
PCT/US2013/046294, International Search Report dated Oct. 8, 2013, 3 pages.
PCT/US2013/046294, Written Opinion of the International Searching Authority dated Oct. 8, 2013, 6 pages.

*Primary Examiner* — Mark R Gaworecki
(74) *Attorney, Agent, or Firm* — Conley Rose, P.C.; Kristin Jordan Harkins

(57) ABSTRACT

Embodiments generally relate to detection of end of service life for respirator filter cartridges for organic vapor(s). Typically, detection of end of service life might use a competitive UV absorbance-fluorescence approach. Thus, a sensor that emits light upon application of UV may be placed within the cartridge, with a UV lamp and a light detector directed at the sensor. In some embodiments, a plurality of corresponding sensor and UV lamp and light detector might be used. Typically, the light level emitted by the sensor(s) might be used to estimate effective end of service life.

20 Claims, 4 Drawing Sheets

END OF SERVICE LIFE INDICATOR FOR ORGANIC VAPOR RESPIRATOR FILTER CARTRIDGE

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments may relate generally to devices and/or methods for detection of end of service life for a respirator filter cartridge, and more specifically to detection of end of service life for a filter cartridge for a respirator for organic vapors.

BACKGROUND

Respirators often use filter cartridges to protect a user from potentially hazardous vapors. When the respirator is in place on the user (typically attached to the face or head in a way to form a seal), air is drawn into the respirator through the filter cartridge whenever the user breathes (and air can typically only enter the respirator through the cartridge, so that the air may be filtered by the cartridge to ensure that air breathed in by the user while wearing the respirator is clean and safe). Such filter cartridges typically contain filtering material that can lock up one or more potentially hazardous vapors. As the filtering material is exposed to the vapor, it typically absorbs the vapor molecules through the pore structure of the material. Thus, by their very nature, the filter cartridges have a limited effective lifespan (after which the filtering material has absorbed all it can, and the cartridge cannot filter additional vapor). Once a filter cartridge has reached the end of its service life, it is no longer effective at protecting the user. Then the user should either remove themselves from the environment with hazardous vapors or else replace the filter cartridge on the respirator with a new cartridge. Thus, to effectively protect the user, it can be important to know when to change filters based on the service life of the cartridge.

Organic vapors are one type of potentially hazardous vapor that a respirator might filter; unfortunately, there is currently no commercially available end of service life indicator (ESLI) for organic vapors. Rather, the end of service life is often estimated based on (1) a schedule provided by the manufacturer or (2) the user actually smelling the odor of organic vapor as it penetrates an expired filter cartridge. Both of these approaches are problematic, however, since the schedule is a laboratory estimate and does not take into account the actual conditions experienced by the filter material (which could greatly impact the service life) and since the user would be actually exposed to potentially hazardous organic vapors before being able to smell odor.

Applicants have developed an end of service life indicator (ESLI) for organic vapors, so that an effective estimate of the end of service life for a particular cartridge experiencing a particular organic vapor environment can be determined. This may allow users to effectively replace filters in a safer way (reducing the risk of unintended exposure to potentially hazardous organic vapors).

SUMMARY

Aspects of the disclosure may include embodiments of an effective-end-of-service-life indicator system for a filter cartridge for a respirator for organic vapor, comprising one or more of the following: a sensor, located within the cartridge (often on the inner surface of the cartridge), that fluoresces visible light upon exposure to UV light; a UV lamp operable to emit UV light; and a visible light detector operable to detect the intensity level of visible light; wherein: the UV lamp is directed towards the sensor, and the visible light detector is directed towards the sensor. In some embodiments, the UV light emitted by the UV lamp may be approximately UV 254±10 nm. Some embodiments may further comprise a lens operable to focus UV light onto the sensor located between the UV lamp and the sensor and/or an optical filter operable to filter out wavelengths of light other than visible light located between the sensor and the visible light detector. In some embodiments, effective end of service life may be indicated based on decreasing visible light detected by the visible light detector upon application of UV light from the UV lamp onto the sensor. In some embodiments, the sensor may be located near the front of the cartridge and effective end of service life may be based on visible light decrease corresponding to near-end-of-life usage of cartridge for specific organic vapor environment. In some embodiments, the sensor may comprise one or more of the following: metal dotted zinc silicate, calcium tungstate, calcium silicate, magnesium arsenate, and the dotted metal ions may include one or more of the following: Mn, Zn, Cu, Fe, Sn, Pb, Bi, or Sb. Often embodiments may further comprise absorbent material within the sensor operable to absorb one or more organic vapors, and the absorbent material may comprise one or more of the following: active carbon, Si/Al molecular series, clay, or organic polymer. In some embodiments, the sensor may comprise fluorescent material operable to fluoresce (or stated another way, emit) visible light upon application of UV light and absorbent filter material. Embodiments may further comprise filter material within the cartridge operable to absorb one or more organic vapors. And in some embodiments, the UV lamp and the visible light detector (often both located in a fluorescence reader) may be removably attached to the cartridge.

Other aspects of the disclosure may include embodiments of an effective-end-of-service-life indicator system for a filter cartridge for a respirator for organic vapor, the filter cartridge having a front and a rear, comprising one or more of the following: two sensors, located within the filter cartridge (often on the inner surface of the cartridge), that fluoresce visible light upon exposure to UV light; and two fluorescence readers; wherein: each reader corresponds to one of the sensors; each reader comprises a UV lamp and a visible light detector, the UV lamp of each reader is directed toward the corresponding sensor, the visible light detector of each reader is directed toward the corresponding sensor; and first set of corresponding sensor and reader is located forward in the cartridge, while second set of corresponding sensor and reader is located rearward in the cartridge. In some embodiments, effective end of service life may be indicated based on the rearward reader detecting light level decreasing to approximately the light level detected by the forward reader. For example, in some embodiments effective end of service life may be indicated based on the forward light detector detecting visible light level that is about 0-10% less than the visible light level detected by the rearward light detector. In some embodiments, the first set of corresponding sensor and reader may be located at about 10% position within the cartridge, while the second set of corresponding sensor and reader may be located at about 80% position within the cartridge. And in some embodiments, the UV light emitted by each UV lamp may be approximately UV 254±10 nm. In some embodiments, each sensor may comprise one or more of the following: metal dotted zinc silicate, calcium tungstate, calcium silicate, magnesium arsenate, and the dotted metal ions may include one or more of the following: Mn, Zn, Cu, Fe, Sn, Pb, Bi, or Sb. The system in some embodiments may further comprise filter material within the cartridge operable to absorb one or more organic vapors, wherein the filter material may comprise one or more of the following: active carbon, Si/Al molecular series, clay, or organic polymer.

Additional aspects of the disclosure may include one or more methods of detecting effective-end-of-service-life for a filter cartridge for a respirator for organic vapor having a sensor located therein that fluoresces visible light upon exposure to UV light, comprising one or more of the following: directing UV light towards the sensor; and detecting visible light emitted by the sensor. In some embodiments, the method might further comprise absorbing one or more organic vapors and indicating effective-end-of-service-life for the cartridge based on decreasing visible light level emitted by the sensor upon application of UV light. In some embodiments, indicating effective-end-of-service-life may be based on visible light decrease corresponding to near-end-of-life usage of the cartridge for specific organic vapor environment. In other embodiments, where the filter cartridge comprises a second sensor located therein that fluoresces visible light upon exposure to UV light and wherein the second sensor is located rearward of the first sensor within the cartridge; the method may further comprise: absorbing one or more organic vapors within the cartridge; directing UV light towards the second sensor; detecting visible light emitted by the second sensor, comparing visible light emitted by the first sensor to visible light emitted by the second sensor; and indicating effective-end-of-service-life for the cartridge based on decrease in visible light level emitted by second sensor approaching or reaching visible light level emitted by first sensor.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 7A illustrates an exemplary approach for removably attaching a detection device (or reader) to the body of a filter cartridge, while

DETAILED DESCRIPTION

Figure 1:
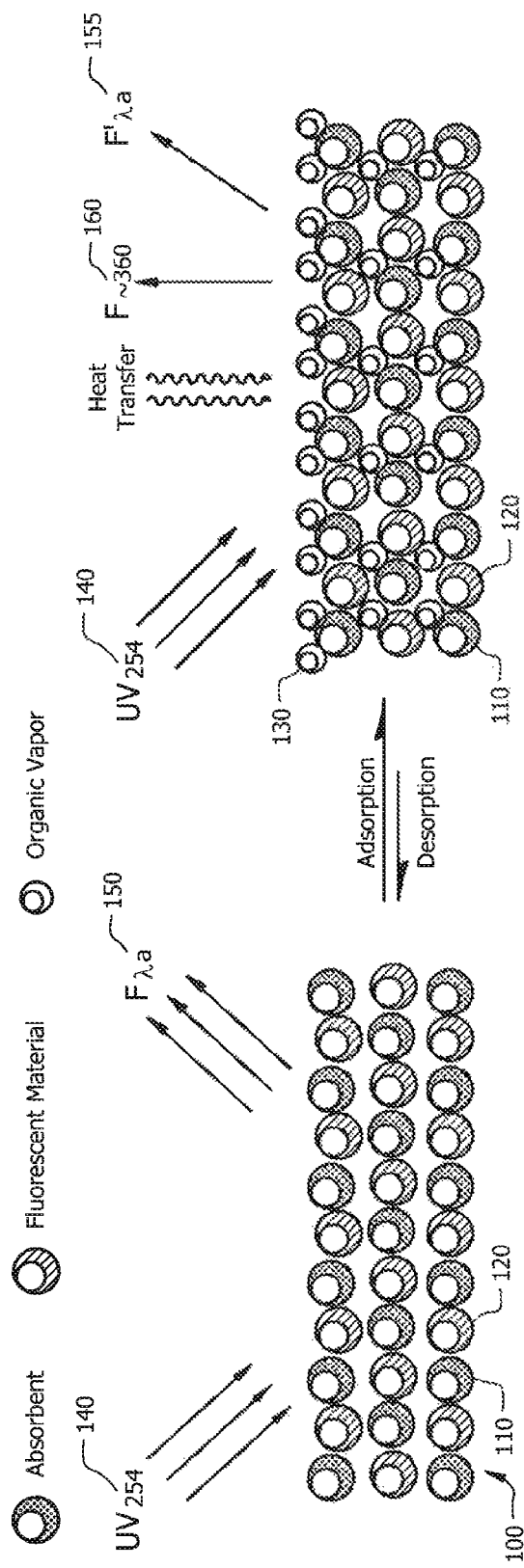
FIG. 1 illustrates a general schematic approach in which organic vapor(s) compete to absorb UV light.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "forward" when used to describe a position within an embodiment means toward or in proximity to the front end of the cartridge, where the front of the cartridge means the end of the cartridge furthest from the attachment to the respirator and therefore furthest from the body of the user. Thus, forward might for example mean away from the user and/or the air intake of the respirator.

The term "rearward" when used to describe a position within an embodiment means toward the rear end of the cartridge, where the rear of the cartridge means the end of the cartridge closest to the attachment to the respirator and therefore closest to the body of the user. Thus, rearward might for example mean toward the user and/or the air intake of the respirator.

The term "effective end of service life" means an estimate of the end of service life of a filter cartridge, when the filter cartridge will no longer effectively absorb organic vapors and offer adequate protection for a respirator user in an environment with organic vapors; the estimate may include a margin of error or safety margin and typically would allow a user to be warned to replace the filter cartridge while there is still some life in the cartridge.

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Disclosed embodiments generally relate to methods, as well as devices for implementing such methods, for determining effective end of service life for a filter cartridge for a respirator for organic vapors. In considering ways to measure the service life of a filter cartridge for a respirator to be used for organic vapors, Applicants noted that organic vapors tend to absorb UV light. This led Applicants to wonder if UV light absorption could somehow be used to estimate the amount of organic vapor absorbed by a filter cartridge and/or the remaining effective life of the cartridge. Applicants considered a model in which a sensing material that also absorbs UV light (in competition with the organic vapors) might be included in the filter cartridge. If the amount of UV light being absorbed by this sensing material could be measured, it might perhaps be possible to correlate that information in a way to estimate the effective end of service life. In other words, the sensing material (that may somehow be incorporated into a cartridge) would tend to absorb less UV light when there is more organic vapor present in the cartridge material, since the organic vapor would absorb the same UV light as the sensing material (thereby reducing the amount of UV light available to be absorbed by the sensing material). Applicants developed a sensing material that absorbs UV light and fluoresces based on the amount of UV light absorbed (typically in a fixed proportion). The sensing material might, for example, include absorbent material (which may be similar to the filter material of the cartridge) and fluorescent material (which may fluoresce light of a specific wavelength range upon application of UV light). By locating this sensing material within the cartridge, it can work in competition with any absorbed organic vapors, and the amount of fluorescence (typically visible light) emitted by the sensing material upon exposure to UV light might give some indication of the amount of organic vapor absorbed in the cartridge. This fluorescence could then be detected using a light intensity reader, for example, which would allow for estimation of absorbed organic vapor. In other words, detection of end of service life might use a competitive UV absorbance-fluorescence approach.

Organic vapors typically absorb UV light in the range of about 254±10 nm (and some of these vapor molecules might also emit fluorescence at a wavelength of about 360 nm). Thus to be effective, the sensing material typically would absorb UV light in approximately the same range as the organic vapor (i.e. 254±10 nm) but emit fluorescence at a different wavelength than the organic vapor (often in the visible light range and typically greater than 360 nm, or alternatively greater than about 450 nm, for example, the sensing material might fluoresce at about 525±10 nm in some embodiments). The wavelength emissions by the organic vapors may then be filtered out and/or the reader may be designed to not detect those wavelengths (for example, the reader might be operable to detect only long wavelength emissions such as visible light). Additionally, this competitive approach might work best if the sensing material fluoresces at a wavelength (typically about 525±10 nm) that is not in the range of UV (and thus is not absorbed by the absorbent material and/or organic vapor) and if absorbed organic vapor and/or absorbent material do not fluoresce at a similar wavelength (so that the fluorescence at the designated (long wave) wavelengths can effectively relate to the amount of UV light absorbed by the sensing material and thereby be correlated to the amount of organic vapors present in the cartridge).

FIG. 1 illustrates an exemplary schematic diagram of such an organic vapor sensing approach. The sensor 100 may comprise an absorbent material 110, which may typically be similar to the filter material of the cartridge, that absorbs organic vapor 130, and a fluorescent material 120, which may absorb UV light 140 and fluoresce as a result. When UV light 140 is directed onto the sensor 100 when there is no organic vapor 130 present, it may be absorbed by only the fluorescent material 120. Typically the absorbent material 110 would not absorb UV light 140 in the same range as the organic vapors 130 or the fluorescent material 120, so as not to interfere with the competitive absorbance of the two materials, and the absorbent material 110 typically also would not absorb the fluorescence 150 (typically visible light) that may be emitted by the fluorescent material 120. When the sensor 100 is in the presence of organic vapors 130, the organic vapors 130 may be absorbed by the absorbent material 110 and may begin to absorb UV light 140 that may be directed toward the sensor 100. The intensity of fluorescence (such as visible light) 150 emitted from the fluorescent material 120 of the sensor 100 upon application of UV light 140 will typically decrease when the concentration of organic vapors 130 absorbed in the filter increases (due to the competition for UV light absorption). In other words, the fluorescence 155 by the fluorescent material when organic vapors 130 are present will typically be less than the fluorescence 150 by the fluorescent material in the absence of organic vapors 130. Thus, a difference may be detectable between the fluorescence before organic vapor was absorbed 150 and after organic vapor begins to absorb 155 (where the numbers of arrows in the diagram of FIG. 1 represent intensity). Therefore, a change in fluorescence intensity reading from the fluorescent material in the sensor may be used to provide some indication of the concentration of organic vapors absorbed in the filter material of the cartridge. Thus, FIG. 1 illustrates generally the principle of competitive absorbance/fluorescence.

Figure 2:
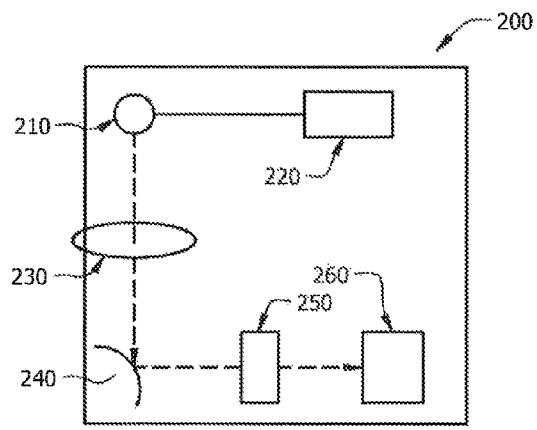
FIG. 2 illustrates schematically an embodiment of a system for detecting absorbed organic vapor(s) and estimating end of service life.

Applicants have developed embodiments to put the general principle described above into practical use for estimating the effective end of service life for a filter cartridge for a respirator. FIG. 2 illustrates schematically an embodiment of such an end of service life indicator device/system. As shown in the embodiment of FIG. 2, the system may comprise a sensor 240 (typically located within the filter cartridge), a UV lamp 210 that would typically emit UV light (such as UV 254±10 for example) that may be directed at the sensor 240, and a light detector 260 that may detect the visible light emitted by the sensor 240. The UV lamp may be powered by a battery or other power source 220. Typically the UV lamp emits UV of a known/fixed wavelength (for example UV 254±10 nm) at a known/fixed intensity (for example about 1 mW). The intensity of the light emitted by the UV lamp 210 may be held constant using an electronic design for the power source 220 that could ensure a stable voltage is provided to the UV lamp 210 at all times during its use. Some embodiments may also include one or more optional features such as a lens 230 (operable to focus UV rays from the UV lamp 210 onto the sensor 240) located between the UV lamp 210 and the sensor 240, an optical filter 250 (operable to filter out other frequencies (e.g. light emitted by the organic vapors)) located between the sensor 240 and the visible light detector 260, a processor/circuitry for correlating/translating the detected light intensity into information regarding amount of absorbed organic vapors and/or end of service life of the cartridge, and/or an alert for warning the user and/or a display for indicating the remaining life of the cartridge. The UV lamp 210 of the system 200 typically would be directed toward the surface of the sensor 240. Further, the visible light detector 260 typically would be directed toward the surface of the sensor 240 so as to detect the fluoresced light (typically about 525±10 nm). An alarm condition (which may indicate effective end of service life) may be indicated by the system based on a decrease in the visible light detected by the light detector 260 from the sensor 240.

Figure 3:
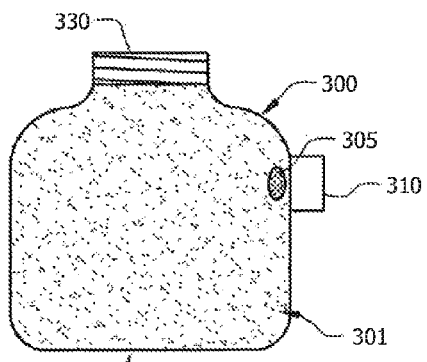
FIG. 3 illustrates a general embodiment of a filter cartridge comprising sensor material and reader unit.

FIG. 3 shows generally an embodiment of a filter cartridge 300 with filtering material 301 having a sensor 305 located therein, with a reader 310 attached to the cartridge. The reader 310 typically includes a UV lamp directed toward the sensor 305, and a light detector directed toward the sensor 305 and operable to detect the light fluoresced by the sensor upon application of the UV light (although in some embodiments, the UV lamp and the light detector could be separate elements individually directed towards the sensor). The sensor 305 is typically located within the cartridge 300 (typically on the inner surface of the cartridge in proximity to the location of the reader and otherwise surrounded by filter material). Often the sensor 305 comprises material that fluoresces upon exposure to UV light (for example UV 254±10 nm) and absorbent material operable to lock up organic vapor(s). The absorbent material typically would not absorb UV light in the same or similar range as the fluorescent material (for example about UV 254±10 nm) or visible light so as not to interfere with the readings. The filter material 301 in the cartridge may be similar to the absorbent material in the sensor 305 and may comprise one of more of the following: active carbon, Si/Al molecular series, clay, or organic polymer. A fixed or known amount/intensity of UV light (for example about 1 mW) may be directed from the reader 310 toward the sensor 305 (i.e. into the cartridge 300) and the visible light intensity emitted by the sensor 305 (for example, light at a long wavelength, typically about 525±10 nm) may be detected by the reader 310. Thus, detection may be accomplished using the reader 310 that may be attached to the cartridge 300. Optionally, the reader 310 may be attached to the cartridge 300 in a removable fashion (so that the reader may be removed and reused in other cartridges once the present cartridge reaches its end of service life). Further, an alarm or warning associated with the decrease in visible light level detected from the fluorescent material of the sensor 305 might be used to alert a user of approaching end of service life. Typically, a decrease in light intensity level detected from the sensor 305 would be used to determine effective end of service life for the cartridge 300. Additionally, when exposed to organic vapor, the filter material 301 in the cartridge 300 may absorb the vapor in such a way that the forward end of the cartridge 320 fills with trapped/absorbed organic vapor before the rearward end of the cartridge 330. Typically, organic vapor may only progress to a more rearward position in the cartridge once the filter material 301 at a more forward position in the cartridge has been used up (for example, the filter material at the forward point no longer has the capacity to absorb additional vapor).

Figure 4:
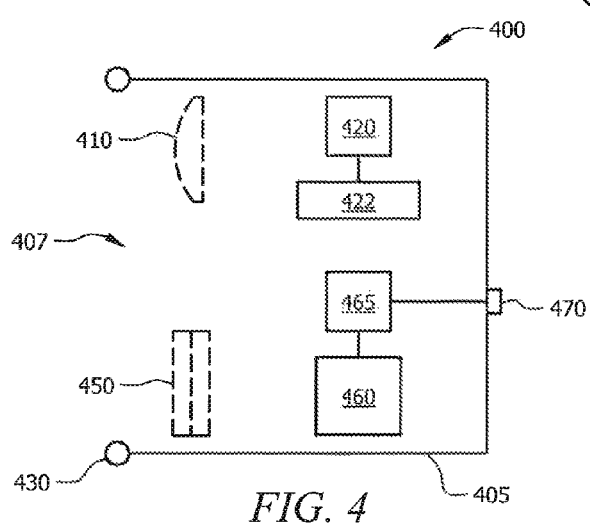
FIG. 4 illustrates a schematic of an exemplary fluorescence reader unit.

FIG. 4 illustrates a schematic of an embodiment of a fluorescence reader 400. The reader 400 includes a UV lamp 420 powered by a power supply 422 (which could be a battery, for example). The UV lamp 420 is directed out of the housing 405 of the reader 400 (typically through an opening 407 in the housing and into a corresponding opening in the cartridge), so that when the reader 400 is in place on the cartridge, the UV lamp 420 is directed towards a sensor within the cartridge. Optionally, a lens 410 may be located in the path of the UV lamp 420. A light detector 460 is also located within the housing 405 of the reader 400. The light detector 460 is directed to detect light emitted by the sensor within the cartridge, with the light typically entering the housing 405 through an opening 407 (where the one of more openings 407 typically align with corresponding openings in the cartridge housing). The housing 405 may have separate openings for the light detector and the UV lamp, or a single opening 407 may function for both elements. The light detector 460 of FIG. 4 detects the type/range of light emitted by the sensor (upon application of UV light) and in the embodiment of FIG. 4 it detects visible light (typically about 525±10 nm). In some embodiments, the light detector 460 is configured to only detect light in a range emitted by the sensor (and not, for example, to detect other wavelengths of light such as light emitted by organic vapors upon application of UV light). In other embodiments, the detector 460 might detect a broader range, and a filter 450 might optionally be located in the path between the sensor and detector. The optional filter 450 could then filter out light that is not in the range of wavelengths emitted by the sensor. The light detector 460 might optionally be electronically connected to a processor 465 that interprets/correlates the detected light intensity to determine the effective end of service life for the cartridge. Also, the reader could optionally include an alert component 470 to notify a user when effective end of service life is reached. This could optionally be a visible alert, such as a light, or an audible alert, such as a beep or audio message. And in the embodiment of FIG. 4, one or more optional seal elements 430 might also be included. The seal 430 might ensure that external light does not interfere with the reading and/or that external air cannot enter the filter cartridge through the opening at the attachment point for the reader 400 (since that might compromise the effectiveness of the cartridge).

In an embodiment, the UV lamp may be driven by about 12 V of power in the form of a battery or other power source, and the UV lamp may provide UV light in the range of about 254±10 nm at an intensity of about 1 mW. The UV light may pass through a lens with a typical diameter of about 10 mm and a typical focal distance of 20 mm and then may be focused onto an area of the surface of a sensor which may have a diameter of about 2 mm. After absorption of the UV light, the sensor may generate a long wavelength (visible) fluorescent emission (typically about 525±10 nm), and the intensity of this emission may be related to the amount of organic vapor absorbed in the sensor material and therefore may relate to the organic vapor absorbed in the cartridge as a whole. The fluorescence emitted by the sensor may be directed through an optical filter (which may have a transmission rate greater than 50% for wavelengths of about 525±10 nm); this filter may remove any light other than the emission from the fluorescent material in the sensor (which may include reflected UV light, emission from the organic vapor, and/or any other light that may interfere with the detection of the fluorescence emission). An optical detector may receive the fluorescent signal and determine the intensity of the fluorescence, which may then be transferred into an electronic signal indicating the amount of organic vapor absorbed in the absorbent material (which typically relates to the amount of organic vapor absorbed by the filter material of the cartridge). The detector may be comprised of one or more silicon photovoltaic cells, which may typically have a diameter of 10 mm and may detect light in the range of 380-680 nm.

Figure 5:
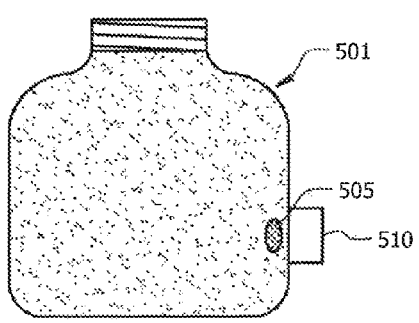
FIG. 5 illustrates an embodiment of an organic vapor detection device typically for use in a known environment.

While the figures above provide some general information about systems and devices for determining effective end of service life, FIGS. 5 and 6 provide more specific examples of two variations of such devices. The embodiment shown in FIG. 5 is an exemplary cartridge sensor device that may be used in a situation when workplace conditions are known and therefore the specific organic vapor(s) to be absorbed by the cartridge are known. In other words, the embodiment shown in FIG. 5 may be vapor/environment specific (for example, using a reader configured for a specific environment, or using a general reader but configuring/setting it based on the specific known environment). The embodiment may comprise a filter cartridge 501 (which may be similar to existing cartridges used for respirators (i.e. may use similar absorbent technology)) with a sensor 505 incorporated into the cartridge (for example, located on the inner surface wall of the cartridge). Typically, the sensor 505 might be located toward the forward end 520 of the cartridge (although in other embodiments the sensor could be located in other positions within the cartridge). So for example, the sensor might be located in the forward 10% of the cartridge or alternatively the sensor may be located in the rearward 10% of the cartridge (i.e. at 90% of the length of the cartridge).

In an embodiment of FIG. 5, a benchmark may be determined based on the performance of the sensor in a controlled environment. An alarm may then be specified based on this benchmark and how it relates to the amount of organic vapor absorbed in the cartridge filter material. So for example, an alarm benchmark might be determined using the following experimental procedure. An exemplary cartridge may be placed in a specific organic vapor environment (i.e. the organic vapor environment being tested). An experimental organic vapor detector (which may only be used for experimental testing purposes to determine a benchmark prior to field use of such a cartridge in a respirator) may be located rearward of the cartridge to determine when the entire cartridge has been saturated with organic vapor (in other words, the experimental organic vapor detector will note when organic vapor begins to pass through the rearward end of the cartridge). Experimental testing may then proceed by directing the tested organic vapor into (the front end of) the cartridge and monitoring the intensity of the fluorescence emitted by the sensor located within the cartridge (typically at a known location). The intensity level emitted by the sensor at the time when the experimental organic vapor detector indicates the presence of organic vapor at the rearward end of the cartridge may then be used to determine a benchmark, which may be, for example, a percentage of the measured intensity level (for example 90%) to indicate near-end-of-service-life. In other words, the intensity of fluorescence from the sensor monitored by the reader at the instant that the experimental organic vapor detector indicates that organic vapor has passed all the way through the filter cartridge (i.e. when the filter cartridge has been entirely used up) should provide an estimate of end of service life for such cartridge when exposed to the tested organic vapor. Effective end of service life might then be set at a specific percentage of the failure level (providing a safety factor). Then, when such a cartridge is used in the field in an environment of the tested organic vapor, a sensor emitting that benchmark light intensity level would indicate effective end of service life of the cartridge. In such a configuration, a benchmark would need to be determined experimentally for whichever organic vapor(s) the filter cartridge would be exposed to (since the benchmark light level may vary depending on the specific organic vapor environment).

In an alternative embodiment, a benchmark light level may be determined by testing the sensor material in a controlled environment and monitoring the emission from the fluorescent material of the sensor when no organic vapors are present. An alarm trigger related to the visible light level emitted from the fluorescent material in the sensor may be determined based on a decrease in visible light level corresponding to near-end-of-service-life (for example, a decrease of 90% of the benchmark light level determined in testing). Alternatively, in another embodiment, the benchmark may be calculated by determining the light level emitted by the sensor material when the absorbent filter material is 90% used up with the organic vapor (i.e. the absorbent material only has 10% the original capacity to absorb additional vapor).

Alarm indication for embodiments may be based on a decrease in visible light level (emitted by the sensor 505) approaching the predetermined benchmark trigger level. In other words, when the visible light level emitted by the sensor 505 (upon application of UV light from the reader 510) and detected by the reader 510 nears or reaches the predetermined benchmark for the given environment (based on the organic vapor(s) present), an alarm may be triggered indicating effective end of service life for the cartridge 501 (giving the user an opportunity to replace the cartridge so that the respirator can continue effectively protecting the user).

Figure 6A:
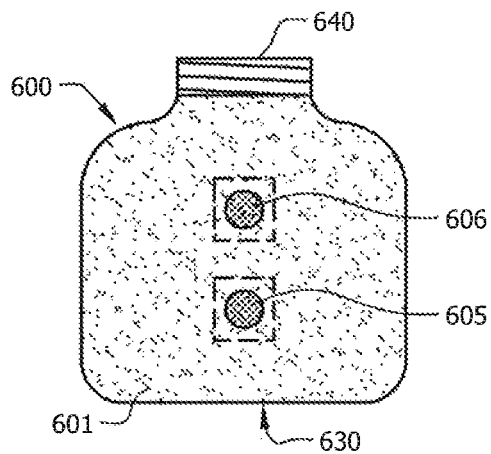
FIGS. 6A-6B illustrate an embodiment of an organic vapor detection device for use regardless of organic vapor environment.
Figure 6B:
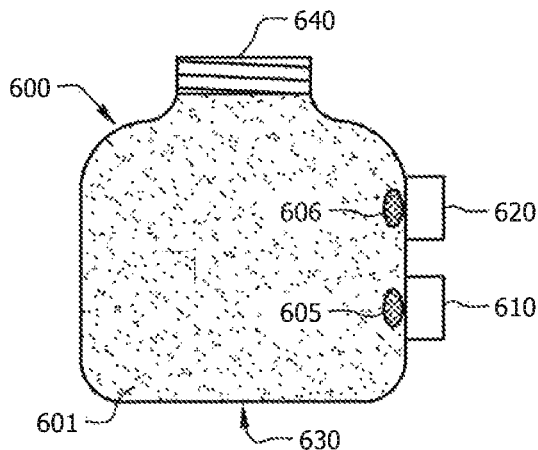
Figure 6C:
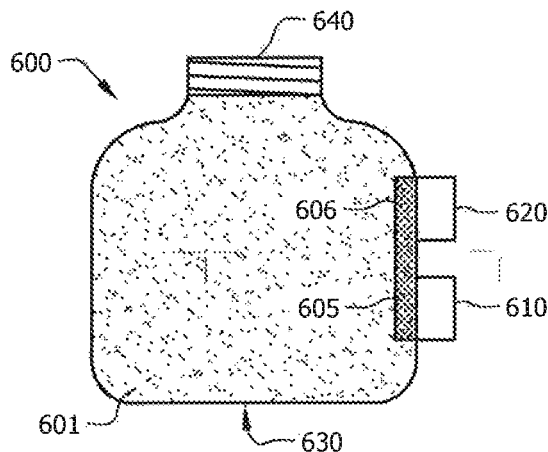
FIG. 6C illustrates an alternative embodiment of an organic vapor detection device for use regardless of the organic vapor environment, with two test sites on a single larger sensor unit.

The embodiments shown in FIGS. 6A-6C are alternative exemplary devices that may be used in a situation when workplace conditions may be known or unknown (and/or constant or changing), and therefore the organic vapor to be absorbed by the cartridge may be known or unknown; in other words, FIGS. 6A-6C show a design that may not be environment-specific and therefore may be used in more general environments and may not require experimental testing/benchmarking of the sensor for a particular organic vapor prior to use in a respirator in the field. As shown in the embodiment of FIGS. 6A-6C, the cartridge 600 may have a front 630 and a rear 640 and may be similar in use to existing cartridges used for respirators (i.e. may use similar absorbent technology). The embodiment of the cartridge may comprise a filter material 601 for trapping organic vapors as well as two or more sensor(s) 605 and 606 located within the cartridge (where the sensor(s) may fluoresce upon exposure to UV light (typically in the range of about 254±10 nm) and emit visible light (for example about 525±10 nm)). The embodiment of FIGS. 6A-6C may also comprise one or more fluorescence reader(s) 610 and 620 that may be attached to the cartridge 600, optionally in a removable fashion.

The embodiment shown in FIGS. 6A-6C may use a comparative method to determine effective end of service life where two or more corresponding sensor/reader combinations may be located within the cartridge 600; one sensor 605 may be at a more forward position (close to the front of the cartridge 630) and the other sensor 606 may be at a more rearward position (close to the rear of the cartridge 640). The system/device may compare visible light emitted by the forward sensor 605 (and detected by the forward reader 610) to visible light emitted by the rearward sensor 606 (and detected by the rearward reader 620). In an embodiment, the sensors may be two separate units located within the cartridge, or alternatively, they may be connected and/or part of a single sensor unit that may have one or more test sites located in forward and rearward positions (with test sites then corresponding to each reader). The term sensor thus shall be considered broad enough to encompass an independent sensor (as shown in FIG. 6B for example), or a test site on a joint sensor unit (as shown in FIG. 6C for example).

In the embodiment shown in FIGS. 6A-6C, the forward sensor 605 may be located towards the front of the cartridge 630 and the rearward sensor 606 may be located towards the rear of the cartridge 640. In one embodiment, the forward sensor 605 may be located at about the 10±2% position (i.e. it is set back from the front of the cartridge 630 about 10% of the overall length of the cartridge 600), and the rearward sensor 606 may be located at about the 80±5% position within the cartridge (i.e. it is set back from the front of the cartridge 630 about 80% of the overall length of the cartridge 600). Further, the reader (620 for example) may indicate end of service life and/or activate an alarm indication when the rearward sensor 606 light level approaches the forward sensor 605 light level (but typically only once organic vapor(s) have been absorbed by the cartridge). In one embodiment, the alarm indication may be activated when visible light emitted by forward sensor 605 is about 0-10% lower than the visible light emitted by the rearward sensor 606 (or alternatively, when the rearward sensor 606 decreases light intensity to be 0-10% above the intensity level emitted by the forward sensor 605). The alarm may be activated in this way because, when the forward sensor 605 begins to become saturated with organic vapor, the light intensity level emitted from the sensor will slow and/or stop decreasing (in other words, the light emitted by the forward sensor at saturation should stabilize at a low intensity level); then, when the rearward sensor 606 starts to approach the same light intensity level as the forward sensor 605, this may indicate it is approaching saturation with the organic vapors as well. More specifically, when the intensity from the rearward sensor is about 0-10% above the intensity from the forward sensor, it may indicated that about 80% of the filter material in the cartridge has been filled with organic vapors. In other words, a comparison of the light intensity level emitted by the forward and rearward sensors may serve to indicate effective end of service life of the cartridge (typically as the light levels are compared and approach one another after organic vapor(s) are being absorbed).

Figure 7A:
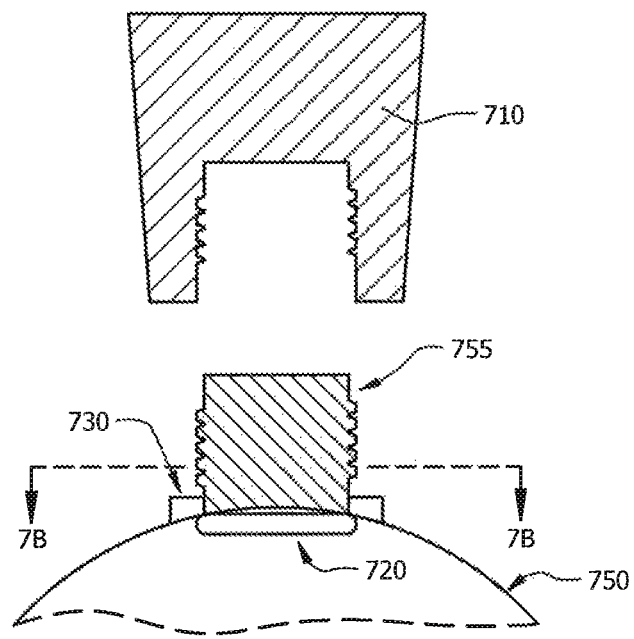
Figure 7B:
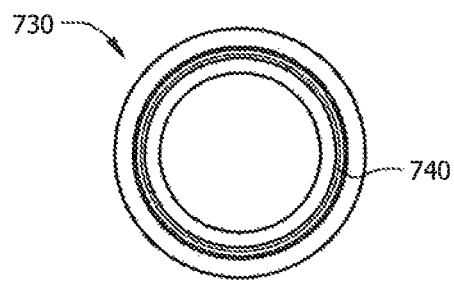
FIG. 7B illustrates a cross-sectional view showing an exemplary sealing ring.

In some embodiments, fluorescence reader(s) may be optionally removably attached to the cartridge. FIG. 7A shows an embodiment of one such exemplary means for attaching a reader to a cartridge. The reader 710 may connect to a projection 755 from the cartridge 750 using corresponding mating threads on both the reader and projection. Typically, the projection 755 might be a hollow tube extending outward from an opening in the cartridge housing. When the reader 710 is attached, the sensor 720 may be located adjacent to the reader 710 so as to interact with the light source (UV lamp) and detector contained therein. In a typical embodiment, the sensor 720 may span the opening of the cartridge housing, so as to provide interaction with the UV lamp and detector and stabilize the sensor 720 in place on the inner surface wall of the cartridge 750 (so for example, the sensor 720 may be attached to the inner surface of the cartridge 750 using an adhesive). When the reader 710 is threaded onto the projection 755 from the cartridge, it may be sealed at the contact point 730 using a sealing ring 740 (as shown in FIG. 7B) or some other sealing means. Sealing may prevent external air from entering the cartridge 750 at the projection point, and may prevent external light from interfering with the reader 710. A removably attached reader may improve the cost effectiveness of the system since when a cartridge is replaced the reader could be reused with another cartridge with sensor material. Typically, even if the reader is removably attached, the sensor is integrated into a cartridge and cannot be easily reused. It might, however, be possible to recycle used cartridges and/or sensors.

In some embodiments, sensor(s) may comprise fluorescent material, absorbent material, and glue, where fluorescent material may comprises one or more of the following: metal dotted zinc silicate, calcium tungstate, calcium silicate, or magnesium arsenate, and wherein the dotted metal ions include one or more of the following: Mn, An, Cu, Fe, Sn, Pb, Bi, or Sb. The absorbent material may be similar to the filter material in the cartridge and may comprise one or more of the following: active carbon, Si/Al molecular series, clay, or organic polymer. The glue typically may not react with organic vapor and may have little or no absorption of UV light (such as UV 254±10 nm for example) and may comprise one or more of the following: CM-Cellulose (CMC), glass water, or CMC-Na. The above three materials for such exemplary sensor(s) may be mixed at a specific ratio, and often may be approximately uniformly dispersed. For example, the glue may be less than about 5% of the sensor material, and the fluorescent material may be less than about 90% of the sensor material (with the remainder typically being absorbent material). Typically the fluorescent material may range from about 0.1% to about 90% of the sensor material, based on the organic vapor(s) to be absorbed by the absorbent material. Typically, the sensor(s) are not significantly affected by humidity.

Another embodiment may include the method of formation of the sensor material, which may be a combination of glue, absorbent material, and fluorescent material. Selection of the fluorescent material may depend on UV absorption, which, for this embodiment, might typically be about 254±10. The fluorescent material may be an organic or inorganic compound, but it should be chemically stable with most organic vapors, and may also be thermally stable (i.e. may resist decomposition at high temperatures) and durable (i.e. may resist breakdown or decomposition over a long period of time). The fluorescent material may typically consist of inorganic material, which may be more stable than organic material, and therefore may be stored for a longer time without experiencing decomposition. Some examples of fluorescent material may include metal dotted zinc silicate, calcium tungstate, calcium silicate, or magnesium arsenate, and wherein the dotted metal ions include one or more of the following: Mn, An, Cu, Fe, Sn, Pb, Bi, or Sb. The selected absorbent material may typically be similar to the filter material of the cartridge and therefore should absorb most organic vapors; also the absorbent material often will not absorb UV or visible light and may comprise one of more of the following: active carbon, Si/Al molecular series, clay, or organic polymer. Selected glue should be thermally stable (i.e. may resist decomposition at high temperatures) and have low or no reaction with organic vapor and low or no absorption at UV 254±10 nm. For example, the glue may comprise one or more of the following: CM-Cellulose (CMC), glass water, or CMC-Na. These materials may then be combined with water and molded into a desired shape under pressure or dry at room temperature. Typically, when forming a sensor, the glue may be less than 5% of the total sensor material and the fluorescent material may be less than 90% of the total sensor material, with the remainder being absorbent material. Often the fluorescent material may range from about 0.1-90% of the total sensor material. The sensor may then be placed within the inside wall of the cartridge.

An embodiment may also include a method for making the device. This may include one or more of the following: forming the sensor (see method above for example), placing the above mentioned sensor within the cartridge (typically by locating the sensor on the inner surface of the cartridge at the attachment location for a reader), and attaching one or more UV lamp(s) and one or more detector(s) to the cartridge, optionally in a removable fashion. Both the UV lamp and detector could be located in a single (reader) unit, and optionally the unit may contain one or more UV lamp(s) and one or more detector(s). When the cartridge must be replaced, the attached UV lamp and detector unit(s) could be removed and optionally attached to a second cartridge having a sensor therein.

An embodiment of a method for detecting absorbed organic vapor(s) and/or estimating end of service life for a filter cartridge for a respirator might include one or more of the following steps: directing UV light towards a sensor in the cartridge and detecting light emitted by the sensor in response to the application of UV light. The UV light would typically be UV 254±10 nm, and the light emitted by the sensor would typically be visible light (for example, greater than 360 nm, or alternatively greater than about 450 nm, typically about 525±10 nm for some embodiments). A reader might be removably attached to the cartridge with the reader having a UV lamp directed toward the sensor and a detector directed towards the sensor. Typically an alarm indication (of effective end of service life) might be based on the decrease in light level from the sensor. In some embodiments, light from the sensor might be filtered before it is detected, so that only visible light will be detected. Often, a benchmark light level may be determined based on a specific organic vapor environment. This benchmark may be determined experimentally by testing a cartridge and sensor in the specific environment and determining the level of intensity when the entire cartridge has been saturated with organic vapor. Then, a percentage of this light level decrease may be used as a benchmark. For example, for a specific organic vapor environment, an alarm might be indicated based on visible light level decreasing to near-end-of-service-life (for example 90% level).

Another embodiment of a method for detecting absorbed organic vapor(s) and/or estimating end of service life for a filter cartridge for a respirator might include one or more of the following steps: directing UV light towards two or more sensors in the cartridge (where the term sensor may encompass an independent sensor, or a test site on a joint sensor) and detecting light emitted by the two or more sensors in response to application of UV light. The UV light would typically be UV 254±10 nm, and the light emitted by the two or more sensors would typically be visible light (greater than 360 nm, or alternatively greater than about 450 nm, typically about 525±10 nm for some embodiments). Typically an alarm indication might be based on the decrease in light level detected from the two or more sensors. In some embodiments, light from the sensors might be filtered before it is detected, so that only visible light will be detected. Often, the two or more sensors might be positioned in the cartridge so that one is located at a more forward position and one is located at a more rearward position. Two or more readers might be removably attached to the cartridge with the readers having a UV lamp directed toward a corresponding sensor and a detector directed towards the same corresponding sensor. When the cartridge has begun to absorb organic vapors, the detected light emitted by the two or more sensors may then be compared, and an alarm (or other indication of effective end of service life) might be indicated based on the level of light detected from the more rearward sensor nearing or reaching the level of light detected from the more forward sensor (for example, within 0-10%). The alarm (indicating effective end of service life for example) may somehow be configured to only alert the user after the cartridge has begun to absorb organic vapors to avoid activation of the alarm when the two sensors are emitting the initial level of intensity, which would be equal or close to equal (since there would be no absorbed organic vapor to cause a disparity initially). Once organic vapor(s) have been absorbed by the cartridge, however, a comparison of the light levels emitted by the forward and rearward sensors might allow for estimation of effective end of service life.

An embodiment may also include a method for using the device, wherein the cartridge containing the sensor material may be attached to a respirator, and a UV lamp and detector unit may be attached to the cartridge in a location that will enable interaction with the sensor material. The respirator may then be placed on the user as is standard/recommended for respirator use. The user may employ the respirator in an environment containing one or more organic vapors. At some point during the use of the respirator, the device may alert the user with a warning referencing the approach of end of service life of the cartridge and approaching unsafe conditions if use of the cartridge is continued. The user may then remove themselves from the environment and may change/replace the cartridge in the respirator. The reader/detector unit, if removably attached to the cartridge, may then be removed from the used cartridge and possibly reattached to a new cartridge.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An effective-end-of-service-life indicator system for a filter cartridge for a respirator for organic vapor, comprising:
    a sensor, located within the cartridge, that fluoresces visible light upon exposure to UV light;
    a UV lamp operable to emit UV light; and
    a visible light detector operable to detect the intensity level of visible light;
wherein;
    the UV lamp is directed towards the sensor; and
    the visible light detector is directed towards the sensor to detect sensor fluorescence.

2. The system of claim 1 wherein the UV light emitted by the UV lamp is approximately UV 254.

3. The system of claim 1 further comprising a lens operable to focus UV light onto the sensor located between the UV lamp and the sensor and an optical filter operable to filter out wavelengths of light other than visible light located between the sensor and the visible light detector.

4. The system of claim 1 wherein effective end of service life is indicated based on decreasing visible light detected by the visible light detector upon application of UV light from the UV lamp onto the sensor.

5. The system of claim 4 wherein the sensor is located near the front of the cartridge and wherein effective end of service life is based on visible light decrease corresponding to near-end-of-life usage of cartridge for specific organic vapor environment.

6. The system of claim 1 wherein the sensor comprises one or more of the following: metal dotted zinc silicate, calcium tungstate, calcium silicate, magnesium arsenate, and wherein the dotted metal ions include one or more of the following: Mn, Zn, Cu, Fe, Sn, Pb, Bi, or Sb.

7. The system of claim 1 wherein the sensor comprises absorbent material operable to absorb one or more organic vapors, wherein the absorbent material comprises one or more of the following: active carbon, Si/Al molecular series, clay, or organic polymer; and wherein the sensor further comprises fluorescent material operable to fluoresce visible light upon application of UV light.

8. The system of claim 1 further comprising filter material within the cartridge operable to absorb one or more organic vapors.

9. The system of claim 1 wherein the UV lamp and the visible light detector are removably attached to the cartridge.

10. An effective-end-of-service-life indicator system for a filter cartridge for a respirator for organic vapor, the filter cartridge having a front and a rear, comprising:
    two sensors, located within the filter cartridge, that fluoresce visible light upon exposure to UV light; and
    two fluorescence readers;
wherein:
    each reader corresponds to one of the sensors;
    each reader comprises a UV lamp and a visible light detector;
    the UV lamp of each reader is directed toward the corresponding sensor;
    the visible light detector of each reader is directed toward the corresponding sensor to detect sensor fluorescence; and
    first set of corresponding sensor and reader is located forward in the cartridge, while second set of corresponding sensor and reader is located rearward in the cartridge.

11. The system of claim 10 wherein effective end of service life is indicated based on the rearward reader detecting light level decreasing to approximately the light level detected by the forward reader.

12. The system of claim 11 wherein effective end of service life is indicated based on the forward light detector detecting visible light level that is about 0-10% less than the visible light level detected by the rearward light detector.

13. The system of claim 10 wherein the first set of corresponding sensor and reader is located at about 10% position within the cartridge, while the second set of corresponding sensor and reader is located at about 80% position within the cartridge.

14. The system of claim 10 wherein the UV light emitted by each UV lamp is approximately UV 254.

15. The system of claim 10 wherein each sensor comprises one or more of the following: metal dotted zinc silicate, calcium tungstate, calcium silicate, magnesium arsenate, and wherein the dotted metal ions include one or more of the following: Mn, Zn, Cu, Fe, Sn, Pb, Bi, or Sb.

16. The system of claim 10 wherein the sensor comprises fluorescent material operable for fluorescing visible light upon application of UV light and further comprises absorbent material operable to absorb one or more organic vapors, wherein the absorbent material comprises one or more of the following: active carbon, Si/Al molecular series, clay, or organic polymer.

17. A method of detecting effective-end-of-service-life for a filter cartridge for a respirator for organic vapor having a sensor located therein that fluoresces visible light upon exposure to UV light, comprising:
    directing UV light towards the sensor; and
    detecting visible light emitted by sensor fluorescence.

18. The method of claim 17 further comprising absorbing one or more organic vapors and indicating effective-end-of-service-life for the cartridge based on decreasing visible light level emitted by the sensor upon application of UV light.

19. The method of claim 18 wherein indicating effective-end-of-service-life is based on visible light decrease corresponding to near-end-of-life usage of the cartridge for specific organic vapor environment.

20. The method of claim 17 wherein the filter cartridge comprises a second sensor located therein that fluoresces visible light upon exposure to UV light and wherein the second sensor is located rearward of the first sensor within the cartridge; the method further comprising:
    absorbing one or more organic vapors within the cartridge;
    directing UV light towards the second sensor;
    detecting visible light emitted by the second sensor;
    comparing visible light emitted by the first sensor to visible light emitted by the second sensor; and indicating effective-end-of-service-life for the cartridge based on decrease in visible light level emitted by second sensor approaching or reaching visible light level emitted by first sensor.

* * * * *